(12) United States Patent
Nishimura et al.

(10) Patent No.: US 8,293,194 B2
(45) Date of Patent: Oct. 23, 2012

(54) ANALYZER

(75) Inventors: Hideki Nishimura, Kyoto (JP); Yasushi Dobuchi, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 12/450,467

(22) PCT Filed: Mar. 26, 2008

(86) PCT No.: PCT/JP2008/055792
§ 371 (c)(1),
(2), (4) Date: May 20, 2010

(87) PCT Pub. No.: WO2008/126682
PCT Pub. Date: Oct. 23, 2008

(65) Prior Publication Data
US 2010/0276286 A1      Nov. 4, 2010

(30) Foreign Application Priority Data

Mar. 28, 2007   (JP) ................................. 2007-086095

(51) Int. Cl.
*G01N 15/06* (2006.01)
*G01N 33/00* (2006.01)
*G01N 33/48* (2006.01)

(52) U.S. Cl. ...... 422/544; 422/50; 422/68.1; 422/82.01; 422/82.02; 436/43

(58) Field of Classification Search ............ 422/50, 422/68.1, 82.01, 82.02; 436/43
See application file for complete search history.

(56) References Cited

U.S. PATENT DOCUMENTS

| 7,183,508 | B2 | 2/2007 | Kasai | |
|---|---|---|---|---|
| 2003/0111357 | A1* | 6/2003 | Black | 205/775 |
| 2005/0284758 | A1* | 12/2005 | Funke et al. | 204/403.02 |
| 2007/0144918 | A1* | 6/2007 | Hsu et al. | 205/775 |

(Continued)

FOREIGN PATENT DOCUMENTS

CN       1453580 A      11/2003

(Continued)

OTHER PUBLICATIONS

International Search Report mailed on Jul. 15, 2008.

(Continued)

*Primary Examiner* — Brian J Sines
(74) *Attorney, Agent, or Firm* — Rader, Fishman & Grauer PLLC

(57) ABSTRACT

The present invention relates to an analyzing device to be used by inserting an analytical instrument 2 comprising a plurality of terminal portions 25A to 28A therein, the device including a plurality of terminals 42 and 43 having a shape of a flat spring to be in contact with the plurality of terminal portions 25A to 28A, and a disposal mechanism for disposing of the analytical instrument 2 after completing an analysis. Contact portions 46 and 47 in the plurality of terminals 42 and 43 having a flat-spring shape to be in contact with the plurality of terminal portions 25A to 28A are placed to be in non-parallel with a direction orthogonal to a disposal direction D1 of the analytical instrument 2 in planar view. The portions 46 and 47 in the plurality of terminals 42 and 43 having the flat-spring shape are preferably placed so as to have a symmetrical or substantially symmetrical positional relationship relative to a center line L1 of the analytical instrument 2 extending along the disposal direction D1.

14 Claims, 13 Drawing Sheets

U.S. PATENT DOCUMENTS

2007/0249921 A1* 10/2007 Groll et al. .................. 600/347
2007/0266871 A1* 11/2007 Wegner et al. ............... 101/395

FOREIGN PATENT DOCUMENTS

| CN | 1790831 A | 6/2006 |
|---|---|---|
| JP | 2001-033418 A | 2/2001 |
| JP | 2003-114213 A | 4/2003 |
| JP | 2004-004057 A | 1/2004 |
| JP | 2006-302541 A | 11/2006 |
| TW | 507400 B | 10/2002 |

OTHER PUBLICATIONS

Office Action issued in corresponding Taiwanese application No. 097111555, dated Mar. 2, 2012.

* cited by examiner

FIG.6
FIG.6A
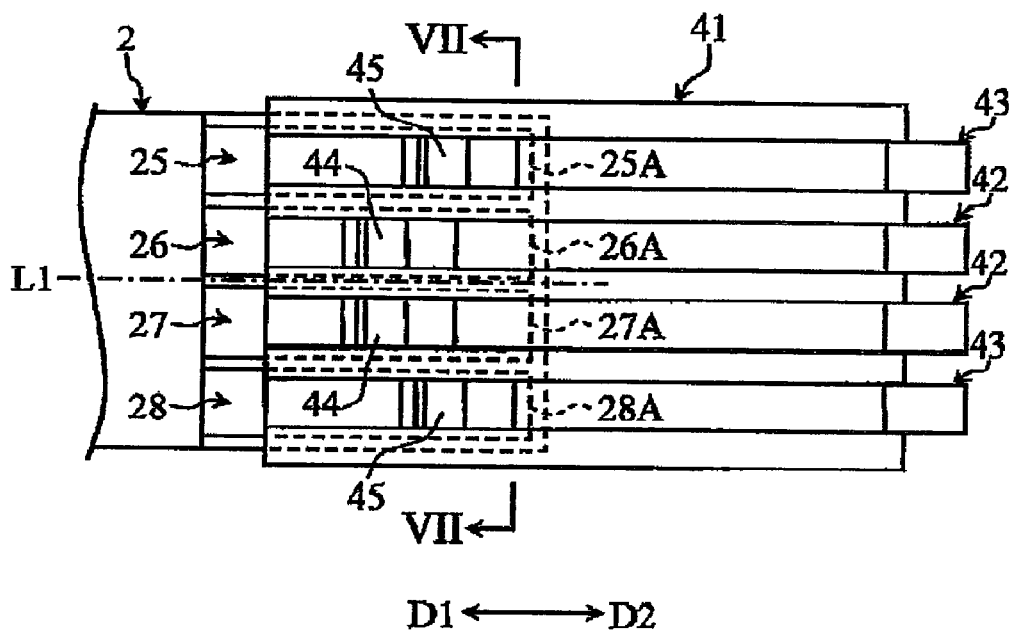
FIG.6B
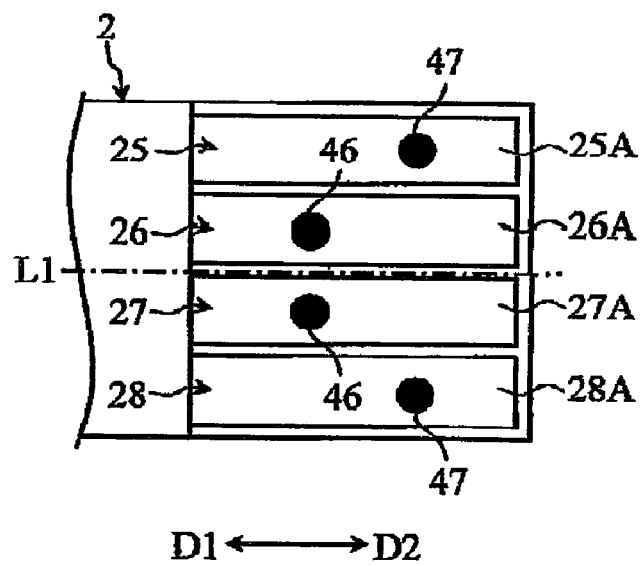

FIG.8
FIG.8A
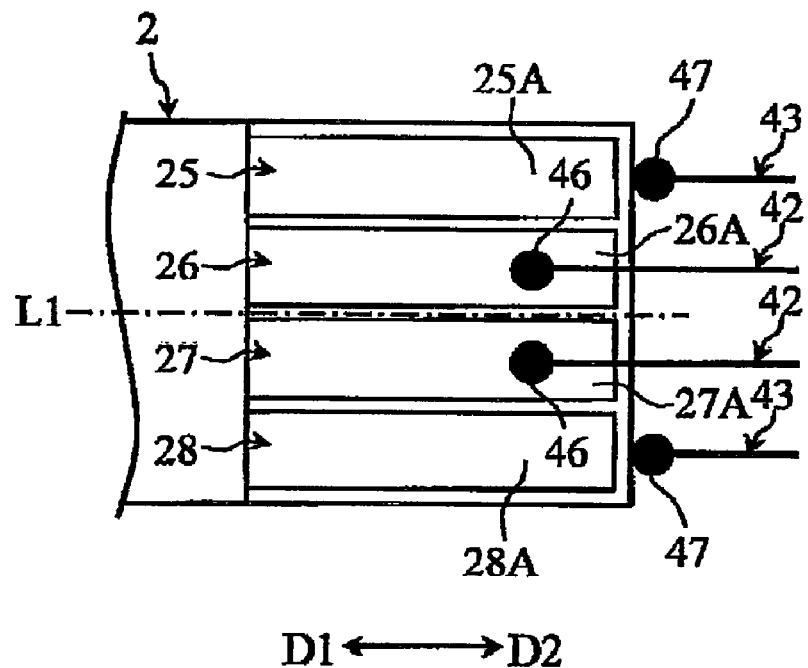
FIG.8B
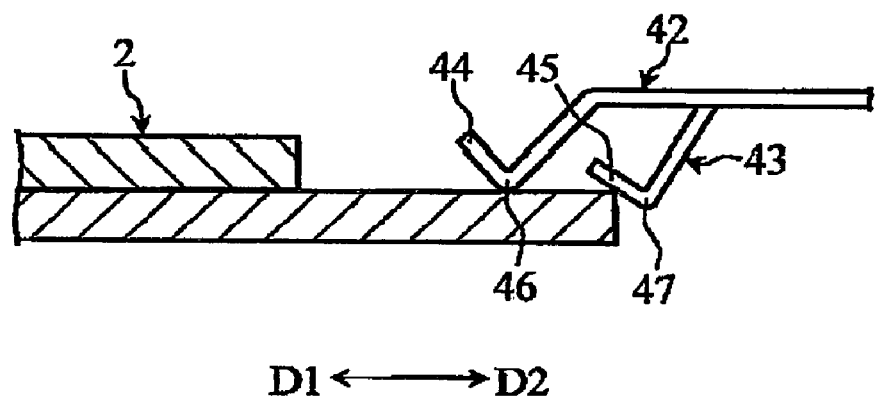

FIG.9
FIG.9A
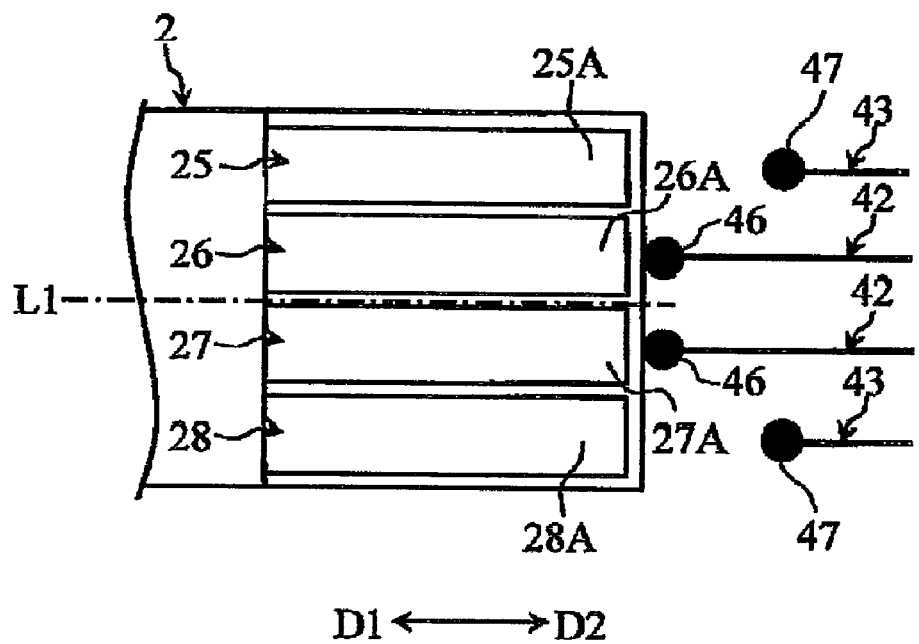
FIG.9B
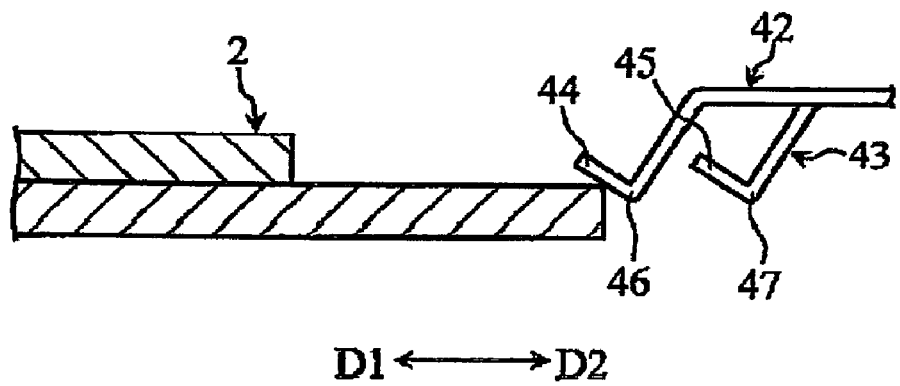

FIG.10
FIG.10A
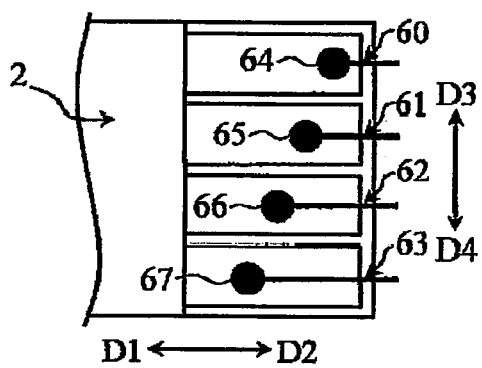
FIG.10B  FIG.10C
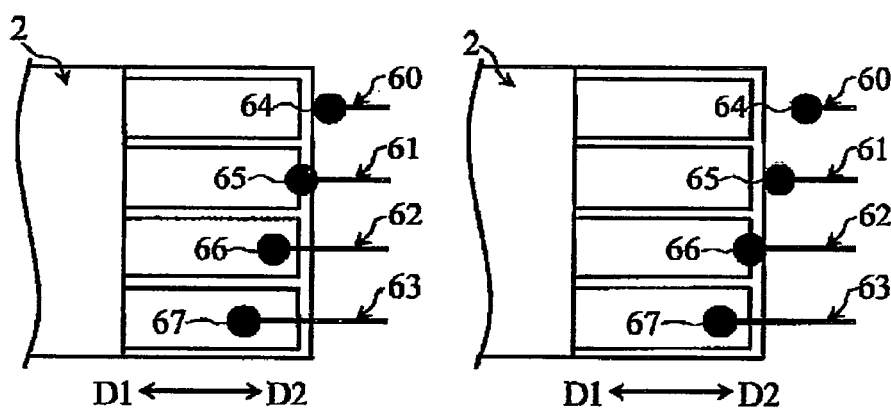
FIG.10D  FIG.10E
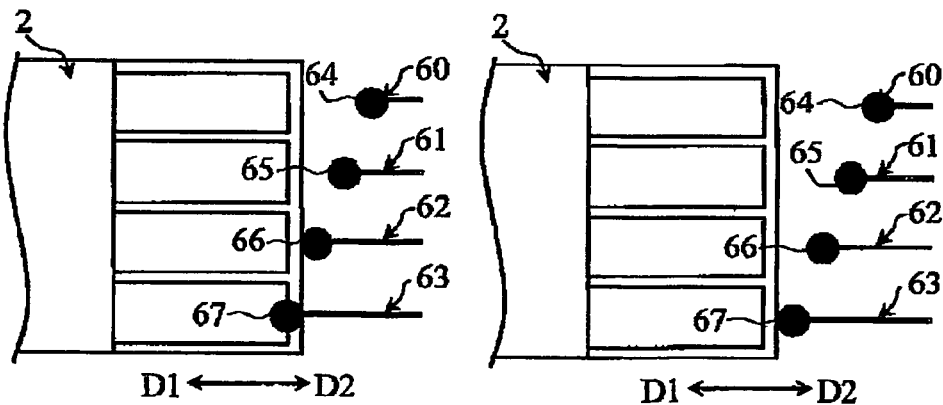

FIG.11
FIG.11A
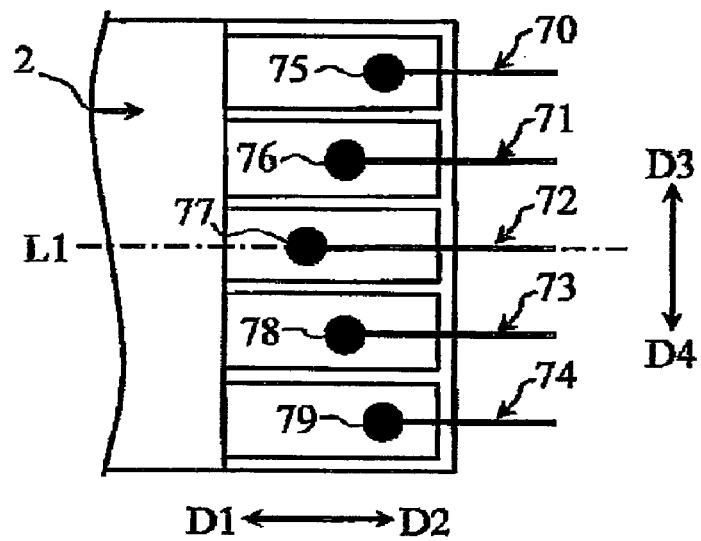
FIG.11B
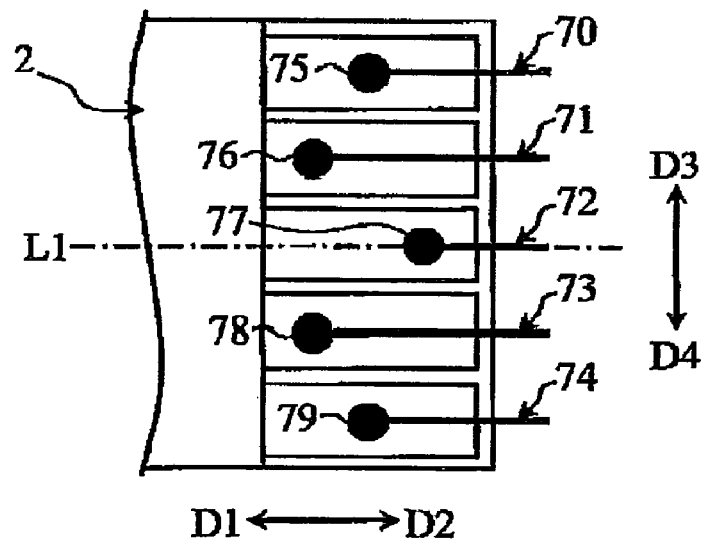

FIG.12
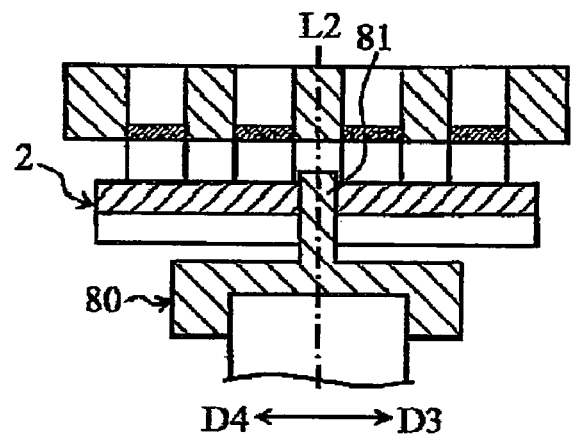
FIG.12A
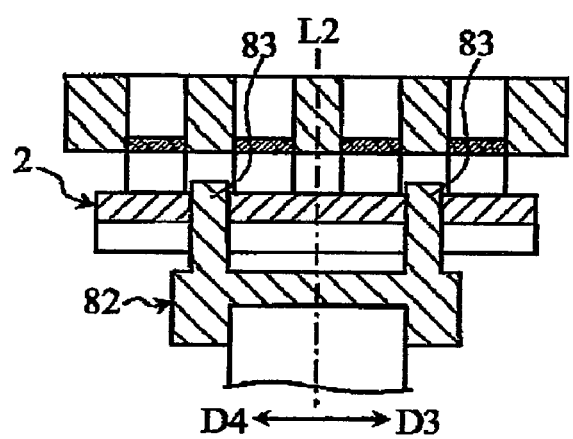
FIG.12B
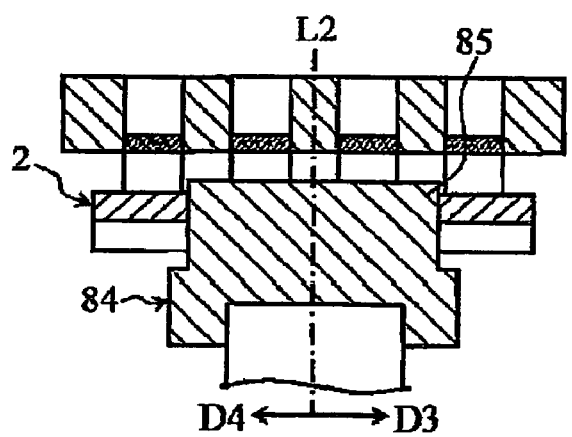
FIG.12C

FIG.15
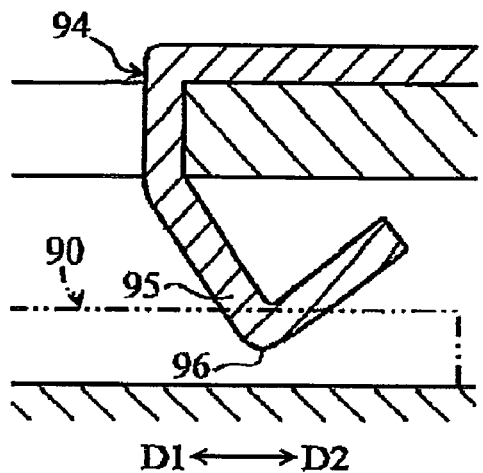
FIG.15A
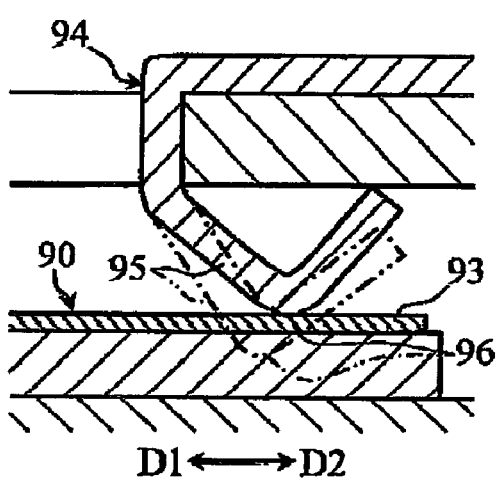
FIG.15B
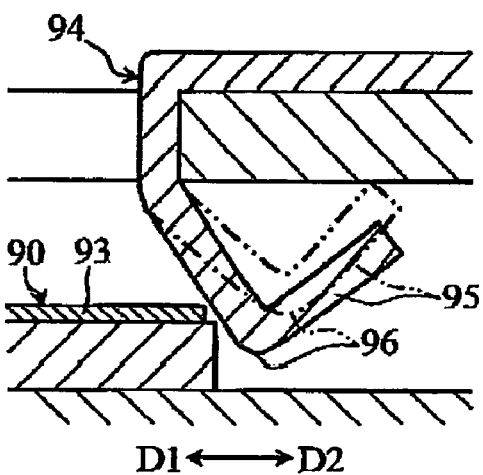
FIG.15C

ANALYZER

TECHNICAL FIELD

The present invention relates to an analyzing device to be used by loading an analytical instrument therein, the analyzing device including a disposal mechanism for disposing of the analytical instrument after completing an analysis.

BACKGROUND ART

In some of the conventionally available methods for measuring a blood glucose level, an analytical instrument is used. In an example of the method, a user inserts the analytical instrument into a portable blood glucose level measuring device, and drips blood on the analytical instrument so that a glucose level of the blood can be automatically measured in the blood glucose level measuring device.

Some of the methods for measuring the blood glucose level employ an electrochemical process. In a case where the electrochemical process is employed in the measurement of the blood glucose level, the analytical instrument is provided with electrodes used for voltage application, while the blood glucose level measuring device is adapted to apply a voltage to the electrodes of the analytical instrument and measure a response current generated then.

In an example of the blood glucose level measuring devices which were proposed so far, a mechanism for disposing of the analytical instrument is provided as illustrated in FIG. 13 so that the user can remove the analytical instrument from the blood glucose level measuring device without any contact with the analytical instrument (for example, see the Patent Documents 1 and 2)

A blood glucose level measuring device 9 illustrated in the drawing is adapted to analyze a specimen using an analytical instrument 90 according to the electrochemical process, and includes a connector portion 91 and an operation knob 92.

As illustrated in FIGS. 13 and 14, the connector portion 91 serves to retain the analytical instrument 90 and includes a plurality of terminals 94 to be in contact with electrodes 93 of the analytical instrument 90. The plurality of terminals 94 apply a voltage to the electrodes 93 of the analytical instrument 90 and measures a response current generated then. In each of the plurality of terminals 94, an edge portion 95 is formed in a shape of a flat spring and contacts the electrode 93 of the analytical instrument 90 at a contact point 96. These terminals 94 are placed so that the edge portions 95 (contact points 96) are linearly aligned in a direction orthogonal to a disposal direction D1.

The operation knob 92 is used to disposing of the analytical instrument 90 mounted in the connector portion 91 and adapted to be slidable in the D1 and D2 directions. The operation knob 92 includes an acting portion 98 for pushing and thereby transferring the analytical instrument 90.

In the blood glucose level measuring device 9, when the analytical instrument 90 is inserted thereinto through an insertion port 97, the terminals 94 of the connector portion 91 contact the electrodes 93 of the analytical instrument 90. When the contact is made, in the edge portions 95 of the plurality of terminals 94, which are provided in the form of the flat spring, the contact positions 96 thereof to contact the analytical instrument 90 are displaced upward as illustrated in FIGS. 15A and 15B. Accordingly, the electrodes 93 of the analytical instrument 90 are pressed by the edge portions 95 of the terminals 94. Thus, the edge portions 95 (contact points 96) of the terminals 94 and the electrodes 93 of the analytical instrument 90 thereby unfailingly contact with each other. In this state, the voltage can be applied to the electrodes 93 of the analytical instrument 90 retained by the connector portion 91, and the response current can be measured. Then, the blood glucose level measuring device 9 can measure a glucose concentration of the blood (blood glucose level) supplied to the analytical instrument 90 based on the response current.

When the measurement of the blood glucose level is completed, the operation knob 92 is transferred in the D1 direction as illustrated in FIG. 13 so that the analytical instrument 90 can be disposed of from the blood glucose level measuring device 9. More specifically, when the operation knob 92 is transferred in the D1 direction, the acting portion 98 of the operation knob 92 pushes an end surface 99 of the analytical instrument 90, and the operation knob 92 is thereby transferred in the D1 direction. As a result, the analytical instrument 90 is finally pushed out of the device in the D1 direction.

When the analytical instrument 90 is fitted in the device, however, the edge portion 95 (contact point 96) in the plurality of terminals 94 is displaced more upward than in a natural state and energized downward as illustrated in FIG. 15B. Therefore, the edge portion 95 (contact point 96) in the plurality of terminals 94 moves downward as it moves away from the analytical instrument 90 and finally returns to the natural state as illustrated in FIG. 15C during the transportation of the analytical instrument 90 in the D1 direction. As a result, an elastic restoring force of the edge portion 95 of the terminal 94 is exerted to the analytical instrument 90 as a force which pushes the analytical instrument 90 in the D1 direction as the edge portion 95 (contact point 96) in the plurality of terminals 94 moves away from the analytical instrument 90. The contact points 96 of the plurality of terminals 94 are aligned in the direction orthogonal to the disposal direction D1 as described referring to FIG. 14. Therefore, the analytical instrument 90 is subject to a load from each of the plurality of terminals 94 almost at the same time. As an unfavorable outcome thereby caused, the analytical instrument 90 may jump out of the device through the insertion port 97 (see FIG. 13) due to such a large load from the plurality of terminals 94 acting on the analytical instrument 90 in the disposal direction D1.

Further, it is necessary to increase the energizing force of the edge portions 95 of the plurality of terminals 94 to be applied to the analytical instrument 90 in order to suitably retain the analytical instrument 90 in the connector portion 91. As a result, it is necessary for a relatively large load from the acting portion 98 of the operation knob 92 to be applied to the analytical instrument 90 in the D1 direction when the analytical instrument 90 is disposed of. Thus, the analytical instrument 90 is inevitably subject to such a relatively large load from the operation knob 92 in addition to the elastic restoring force from the edge portions 95 when the edge portions 95 (contact points 96) of the plurality of terminals 94 move away. These load and force applied to the analytical instrument 90 consequently push the analytical instrument 90 out of the device through the insertion port 97 more often and farther than expected.

When the analytical instrument 90 thus pops out, it may not be possible to dispose of the analytical instrument 90 as originally planned. The blood contained in the analytical instrument 90 is likely to spatter in a location where it is dropped, which possibly causes infections in people nearby, or one who may pickup and dispose of the analytical instrument 90 possibly touches the blood in the analytical instrument 90 by mistake and suffers from infections.

Patent Literature 1: Japanese Unexamined Patent KOKAI Publication No. 2003-114213

Patent Literature 2: Japanese Unexamined Patent KOKAI Publication No. 2001-33418

DISCLOSURE OF INVENTION

Problem to be Solved by the Invention

A main object of the present invention is to prevent an analytical instrument to be disposed of from jumping out of an analyzing device including a disposal mechanism farther than expected by reducing a load from terminals of the analyzing device acting on the analytical instrument when the disposal mechanism is utilized to dispose of the analytical instrument.

Means for Solving the Problem

The present invention provides an analyzing device to be used by mounting an analytical instrument including a plurality of terminal portions therein, the device including a plurality of terminals formed in a shape of a flat spring to be in contact with the plurality of terminal portions, and a disposal mechanism for disposing of the analytical instrument after completing an analysis, wherein contact portions of the plurality of terminals formed in a flat-spring shape to be in contact with the plurality of terminal portions are placed to be in non-parallel with a direction orthogonal to a direction where the analytical instrument is disposed of in planar view.

The contact portions of the plurality of terminals having the flat-spring shape are placed, for example, so as to have a symmetrical or substantially symmetrical positional relationship relative to a center line of the analytical instrument extending along the disposal direction. The contact portions of the plurality of terminals having the flat-spring shape may be linearly or substantially linearly aligned obliquely in the disposal direction.

The disposal mechanism includes one or a plurality of acting portions made to contact the analytical instrument in order to apply a load directed in the disposal direction to the analytical instrument. The one or plurality of acting portions are preferably placed so that the load can be applied to the analytical instrument symmetrically or substantially symmetrically based on a second center line serving as a reference line, the second center line extending in a thickness direction of the analytical instrument when observed in the disposal direction.

The one acting portion is placed on the second center line, while the plurality of acting portions are placed to be symmetrical or substantially symmetrical to the second center line.

BRIEF DESCRIPTION OF DRAWINGS

FIG. 6A is a planar view illustrating positions of a plurality of terminals in the connector portion relative to a biosensor.

FIG. 6B is a planar view schematically illustrating a relationship between contact points in the plurality of terminals and electrodes of the biosensor.

FIG. 8A is a planar view schematically illustrating the relationship between the contact points in the plurality of terminals and the electrodes of the biosensor during the disposal of the biosensor.

FIG. 8B is a sectional view of the principal structural elements, illustrating the relationship between the plurality of terminals and the electrodes of the biosensor during the disposal of the biosensor.

FIG. 9A is a planar view schematically illustrating the relationship between the contact points in the plurality of terminals and the electrodes of the biosensor during the disposal of the biosensor.

FIG. 9B is a sectional view of the principal structural elements, illustrating the relationship between the plurality of terminals and the electrodes of the biosensor during the disposal of the biosensor.

FIGS. 10A to 10E are planar views schematically illustrating another example of the positions of the contact points in the plurality of terminals relative to the electrodes of the biosensor.

FIGS. 11A and 11B are planar views schematically illustrating still another example of the positions of the contact points in the plurality of terminals relative to the electrodes of the biosensor.

FIG. 12 includes sectional views of FIGS. 12A to 12C each corresponding to FIG. 7 for describing another example of an acting potion of a sliding knob in a disposal mechanism.

FIGS. 15A to 15C are sectional views of the principal structural elements, illustrating a relationship between contact points of the plurality of terminals and terminal portions (electrodes) of the biosensor during the insertion and removal of the biosensor with respect to the analyzing device illustrated in FIG. 13.

EXPLANATION OF REFERENCE NUMERALS

Figure 1:
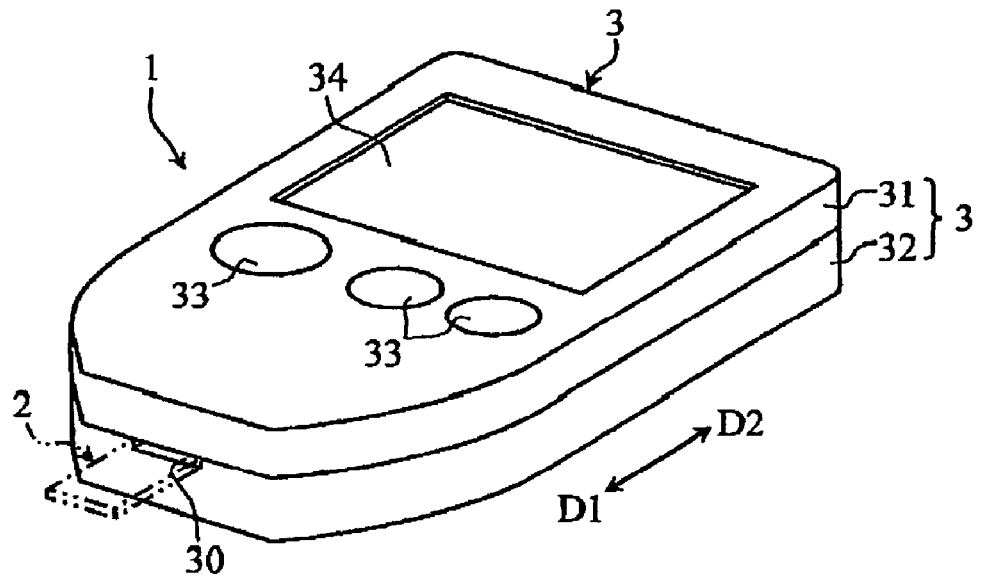
FIG. 1 is an overall perspective view illustrating an example of an analyzing device according to the present invention.

1: blood glucose level measuring device (analyzing device)
25A to 28A: terminal portion (of electrode)
42, 43, 60 to 63, 70 to 74: terminal (terminal having flat-spring shape)
46, 47, 64 to 67, 75 to 79: contact point (of terminal) (contact portion)
5: disposal mechanism
52A, 81, 83, 85: acting portion (of sliding block in disposal mechanism)
D1: disposal direction
L1: center line
L2: (second) center line

BEST MODE FOR CARRYING OUT THE INVENTION

Hereinafter, a blood glucose level measuring device, which is an example of an analyzing device according to the present invention, is described referring to the drawings.

Figure 2:
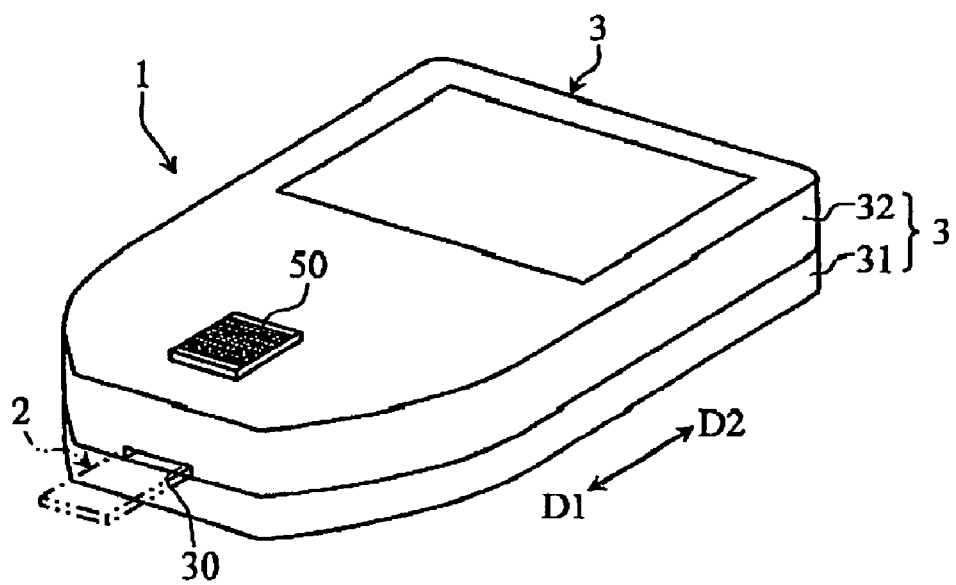
FIG. 2 is an overall perspective view when the analyzing device illustrated in FIG. 1 is observed from the side of a rear surface thereof.
Figure 3:
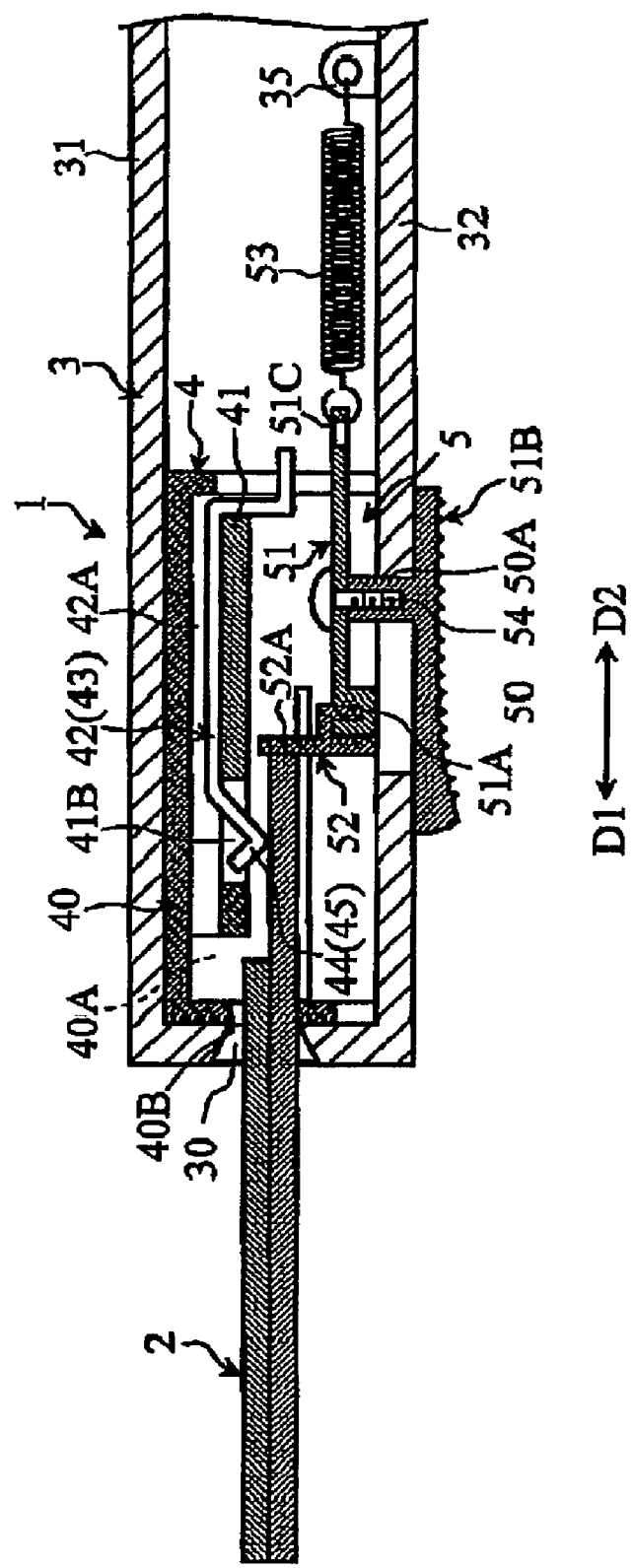
FIG. 3 is a sectional view illustrating principal structural elements of the analyzing device illustrated in FIG. 1.

A blood glucose level measuring device 1 illustrated in FIGS. 1 and 2 is used for analyzing a specimen using a biosensor 2 according to an electrochemical process. The blood glucose level measuring device 1 is a portable device, including a housing member 3, a connector portion 4, and a disposal mechanism 5 as shown in FIG. 3.

Figure 4:
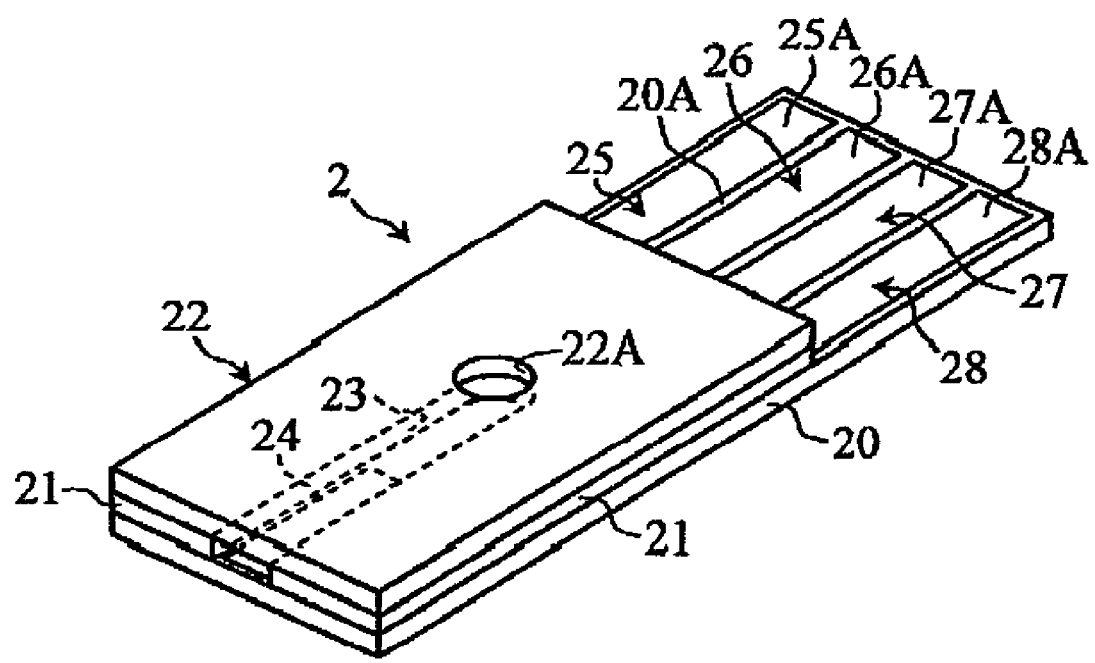
FIG. 4 is an overall perspective view illustrating an example of a biosensor used in the analyzing device illustrated in FIG. 1.

As illustrated in FIG. 4, the biosensor 2 used in the blood glucose level measuring device 1 is disposable, and an overall shape thereof is a flat spring. The biosensor 2 has a structure where a cover 22 is bonded to a substrate 20 having a substantially rectangular shape with a spacer 21 interposed therebetween, and a capillary 23 extending in a longitudinal direction of the substrate 20 is defined by the respective elements 20 to 22.

The capillary 23 transports blood toward an exhaust port 22A of the cover 22 described later by utilizing the capillarity, and also retains the introduced blood therein. Inside the capillary 23, a specimen layer 24 is provided. The specimen layer 24 includes, for example, an electron carrier (complex such as $Ru(NH_3)_6Cl_3$ or $K_3[Fe(CN)_6]$) and oxidoreductase (glucose oxidase (GOD) or glucose dehydrogenase (GDH)).

The spacer 21 is provided to define a distance between the substrate 20 and the cover 22, that is a height dimension of the capillary 23. A double stick tape, for example, constitutes the spacer 21.

The cover 22 includes an exhaust port 22A for discharging gas inside the capillary 23 therefrom. The cover 22 is made of thermoplastic resin having a high wettability such as vinylon or PVA having a high degree of crystallinity.

The substrate 20 is made of an insulating resin material and have a shape larger than that of the cover 22. A plurality of electrodes 25, 26, 27 and 28 (four electrodes in the drawing) are formed on an upper surface 20A of the substrate 20.

The plurality of electrodes 25 to 28 each includes at least a working electrode and a counter electrode for applying a voltage to the blood introduced into the capillary 23. The plurality of electrodes 25 to 28 each further includes a detection electrode for detecting the supply of the blood into the capillary 23, information relating to the biosensor 2 (for example, manufacturing date, manufacturing site and lot number of the biosensor), and an information output electrode for outputting sensor sensitivity (for example, type of analytical curve to be selected) or an electrode to cope with static electricity. The plurality of electrodes 25 to 28 may include an electrode having a different function in addition or in place of one of the detection electrode, information output electrode and static-coping electrode.

It is needless to say that the plurality of electrodes to be provided are not necessarily limited to four electrodes and a different number of electrodes can be designed depending on a purpose. Further, the types of the plurality of electrodes can also be variously changed.

As illustrated in FIGS. 1 to 3, the housing member 3 defines an external shape of the blood glucose level measuring device 1, and serves to house therein the various elements such as the connector portion 4 and the disposal mechanism 5. The housing member 3 includes a sensor insertion port 30 and has a follow structure defined by casings 31 and 32.

The casing 31 is provided with a plurality of operation buttons 33 and a display panel 34. The plurality of operation buttons 33 are used to generate signals for carrying out an analyzing operation and the like and to set various information (for example, to set analysis conditions, to input examinee's ID). The display panel 34 displays an analysis result and an error result, and also displays operation steps and statuses when the information is set. The casing 32 is provided with an operation lever 50 of the disposal mechanism 5 described later.

Figure 5:
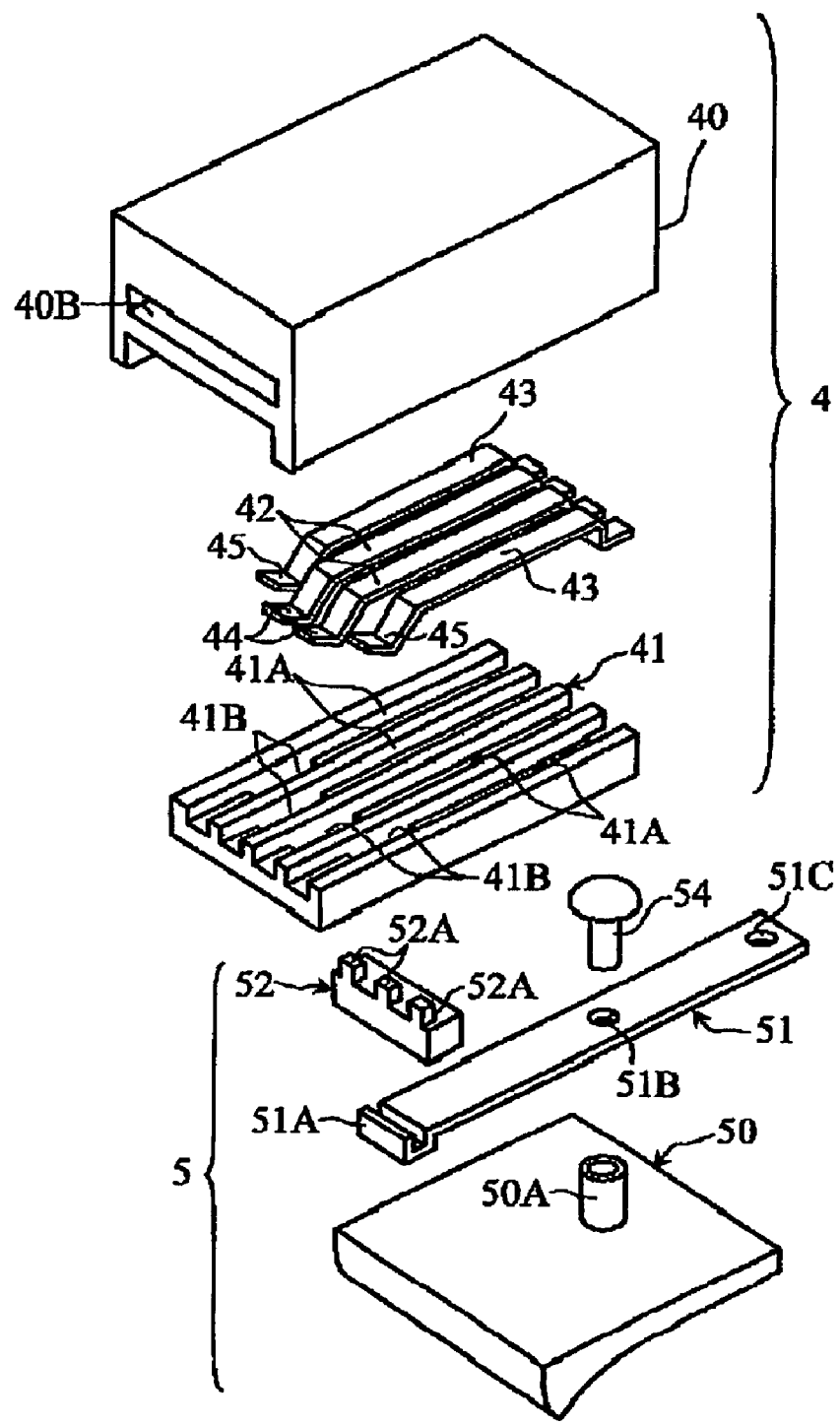
FIG. 5 is an exploded perspective view illustrating a peripheral area of a connector portion in the analyzing device illustrated in FIG. 1.

As illustrated in FIGS. 3 and 5, the connector portion 4 with the biosensor 2 loaded therein, includes a case 40, a terminal platform 41 and a plurality of terminals 42 and 43 (four terminals in the drawing).

The case 40 is adapted to retain the plurality of terminals 42 and 43 and the terminal platform 41, and also retain the biosensor 2. The case 40 includes a hollow portion 40A for retaining the terminal platform 41, and an opening 40B through which the biosensor 2 is inserted and removed.

The terminal platform 41 is provided to secure the plurality of terminals 42 and 43. The terminal platform 41 includes a plurality of slits 41A for housing the terminals 42 and 43, and a through hole 41B from which edge portions 44 and 45 of the terminals 42 and 43 project.

The plurality of terminals 42 and 43 contact terminal portions 25A to 28A of the plurality of electrodes 25 to 28 in the biosensor 2 when the biosensor 2 is loaded in the connector portion 4 (see FIGS. 6A and 6B), and apply the voltage to the plurality of electrodes 25 to 28, and also measures a current value (resistance value) generated at that time. The terminals 42 and 43 with the edge portions 44 and 45 constituted as a flat spring exert a pressing force to the biosensor 2 at contact points 46 and 47 of the edge portions 44 and 45 when the biosensor 2 is fitted into the connector portion 4 and thereby suitably retain the biosensor 2 in the connector portion 4. As illustrated in FIGS. 6A and 6B, the edge portions 44 (contact points 46) in the plurality of terminals 42 and the edge portions 45 (contact points 47) in the plurality of terminals 43 are placed to be symmetrical to a center line L1 of the biosensor 2 extending along the disposal direction D1. The edge portions 44 (contact points 46) in the plurality of terminals 42 and the edge portions 45 (contact points 47) are linearly aligned in a direction in non-parallel with the disposal direction D1.

As illustrated in FIGS. 3 and 5, the disposal mechanism 5 is provided for disposing of the biosensor 2 from the blood glucose level measuring device 1 after the measurement of the blood glucose level is completed. The disposal mechanism 5 includes an operation lever 50, a coupling plate 51, a sliding block 52 and a coil spring 53.

The operation lever 50 is a part to be manipulated to transfer the sliding block 52, and able to reciprocate in the D1 and D2 directions with respect to the housing member 3 in a state where a part of the operation lever 50 is exposed out of the housing member 3 (casing 32). The operation lever 50 is secured to the coupling plate 51 by means of a spring 54 at a female screw portion 50A.

The coupling plate 51 couples the operation lever 50 and the sliding block 52 with each other. The coupling plate 51 includes a crank portion 51A and through holes 51B and 51C. The crank portion 51A is a part which secures the sliding block 52. The spring 54 for securing the operation lever 50 is inserted through the through hole 51B, while an end of the coil spring 53 is engaged with the through hole 51C.

The sliding block 52 is transferred in the D1 and D2 directions in conjunction with the movement of the operation lever 50. When the slicing block 52 is transferred in the D1 direction, the biosensor 2 loaded in the connector portion 4 is also transported. The sliding block 52 includes a plurality of acting portions 52A.

Figure 7:
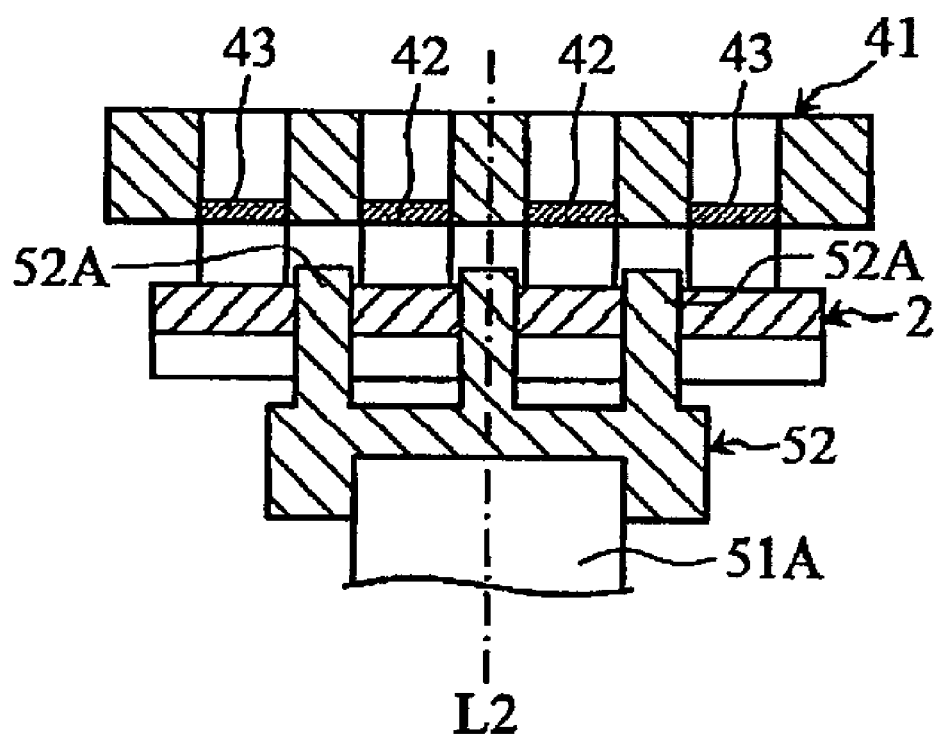
FIG. 7 is a sectional view of FIG. 6A cut along VII-VII line.
Figure 13:
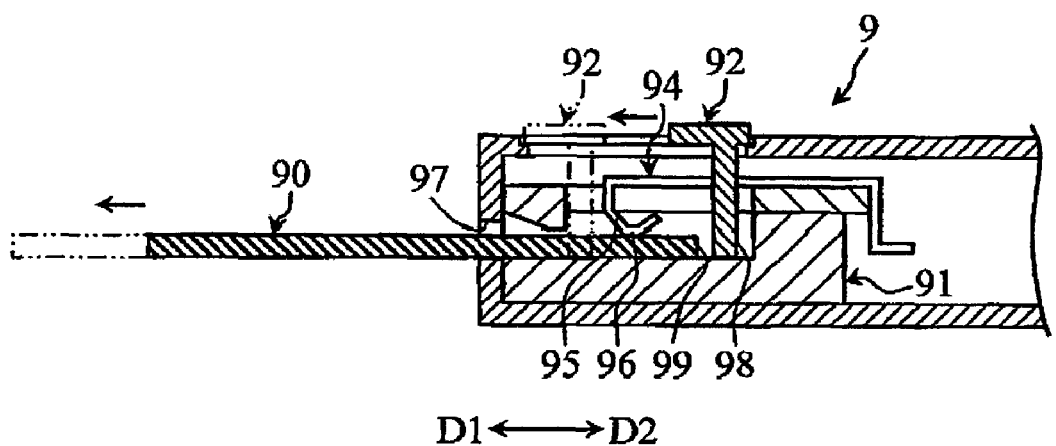
FIG. 13 is a sectional view illustrating principal structural elements of a conventional analyzing device for describing a disposal mechanism provided therein.
Figure 14:
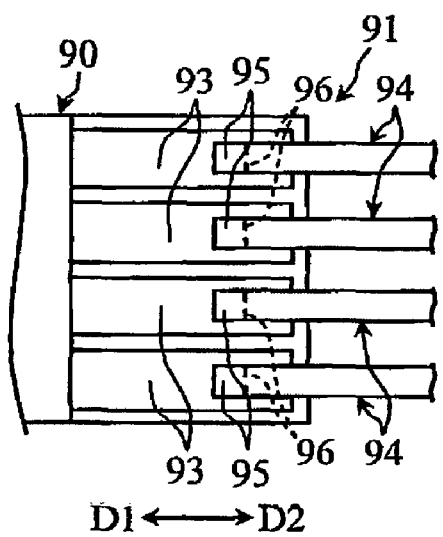
FIG. 14 is a planar view of the positions of a plurality of terminals in a connector portion in the analyzing device illustrated in FIG. 13 relative to electrodes of a biosensor.

The plurality of acting portions 52A contact the biosensor 2 when the biosensor 2 is disposed of from the connector portion 4. As illustrated in FIG. 7, the plurality of acting portions 52A are aligned in a shorter-dimension direction of, the biosensor 2, having a symmetrical positional relationship relative to a center line L2 in the shorter-dimension direction of the biosensor 2.

As illustrated in FIG. 3, the coil spring 53 returns the coupling plate 51, operation lever 50 and sliding block 52 to their standby positions. As described earlier, the one end of the coil spring 53 is engaged with the coupling plate 51, while the other end thereof is engaged with a securing portion 35 of the housing member 3. Therefore, the coil spring 53 is elongated when the load trained in the D1 direction is applied to the operation lever 50 so that the operation lever 50 is transferred in the D1 direction, while the coil spring 53 is constricted when the load acting the operation lever 50 in the D1 direction is released therefrom. After the biosensor 2 is disposed of, therefore, the operation lever 50 and the sliding block 52 are transferred in the D2 direction when the load acting the operation lever 50 in the D1 direction is released therefrom, and then returned to their standby positions.

Next are described a blood glucose level measuring operation using the blood glucose level measuring device 1 and an operation for disposing of the biosensor 2.

As illustrated in FIGS. 1 to 3, when the blood glucose level is measured by the blood glucose level measuring device 1, first, the biosensor 2 is inserted into the blood glucose level measuring device 1. The biosensor 2 is inserted in the blood glucose level measuring device 1 by pushing the biosensor 2 into the connector portion 4 through the sensor insertion port 30. In this case, the terminal portions 25A to 28A of the plurality of electrodes 25 to 28 in the biosensor 2 contact the contact points 46 and 47 of the plurality of terminals 42 and 43 in the connector portion 4, and the biosensor 2 is subject to a pressing force directed downward generated from a spring property of the edge portions 44 and 45 of the terminals 42 and 43. Accordingly, the biosensor 2 is suitably retained in the connector portion 4. The plurality of electrodes 25 to 28 each includes the working electrode and the counter electrode, and the voltage is applied to between the working electrodes and the counter electrodes when the contact points 46 and 47 of the terminals 42 and 43 contact these electrodes.

After the blood is supplied to the biosensor 2, the blood glucose level is measured in the blood glucose level measuring device 1. More specifically, the capillary 23 is filled with the blood supplied to the biosensor 2, and the specimen layer 26 is dissolved. As a result, a liquid phase reaction system is built. Because the voltage is applied to between the working electrodes and the counter electrodes of the plurality of electrodes 25 to 28 at this time, the voltage is also applied to the liquid phase reaction system. Then, the glucose in the blood is reduced by oxidoreductase (electrons are fetched), and the fetched electrons are supplied to the working electrodes by way of an electron carrier. An amount of the electrons supplied to the working electrodes is measured as a response current via the terminals 42 (43) of the connector portion 4. In the blood glucose level measuring device 1, a glucose concentration (blood glucose level) is calculated based on the response current obtained earlier.

When the measurement of the blood glucose level is completed, it is necessary to dispose the biosensor 2. In the blood glucose level measuring device 1, the biosensor 2 is disposed of when the load directed in the D1 direction is applied to the operation lever 50 in the standby state.

When the load directed in the D1 direction is applied to the operation lever 50, the operation lever 50 as well as the coupling plate 51 and the sliding block 52 are transferred in the D1 direction. Along with the transportation of the sliding block 52 in the D1 direction, the plurality of acting portions 52A of the sliding block 52 interfere with the biosensor 2. As a result, the biosensor 2 is pushed by the plurality of acting portions 52A and thereby transferred in the D1 direction as the operation lever 50 is transferred in the D1 direction, and then disposed of through the sensor insertion port 30.

As shown in FIG. 2, when the load acting on the operation lever 50 in the D1 direction is released therefrom, the elastic force of the coil spring 53 pushes the coupling plate 51 as well as the operation lever 50 and the sliding knob 52 in the D2 direction. As a result, the operation lever 50 and the sliding block 52 return to their original positions.

In the blood glucose level measuring device 1, first, the contact points 47 of the terminals 43 move away from the biosensor 2 during the transportation of the biosensor 2 in the D1 direction as illustrated in FIGS. 8A and 8B. Then, the contact points 46 of the terminals 42 move away from the biosensor 2 as illustrated in FIGS. 9A and 9B. More specifically, the plurality of contact points 46 and 47 are positioned to be in non-parallel with the direction orthogonal to the center line L1 of the biosensor 2 and to be symmetrical to the center line L1 of the biosensor 2. Therefore, these contact points do not move away from the biosensor 2 at once, but two each move away from the biosensor 2. Thus constituted, all of the edge portions 44 and 45 in the plurality of terminals 42 and 43 do not exert their elastic restoring force to the biosensor 2 at the same time, but the force of two each acts on the biosensor 2 at a time when the biosensor 2 is disposed of. As a result, too a large load is not applied to the biosensor 2 at once, which prevents the biosensor 2 from jumping out through the sensor insertion port 30. Further, the load in the D1 direction to be inputted to the operation lever 50, that is the load from the sliding knob 52 acting on the biosensor 2 in the D1 direction, is lessened when the biosensor 2 is disposed of because only two of the plurality of contact points 46 and 47 move away from the biosensor 2 at a time. This is also why the load acting on the biosensor 2 in the D1 direction is lessened when the biosensor 2 is disposed of from the blood glucose level measuring device 1. Thus, the biosensor 2 can be easily disposed of from the blood glucose level measuring device 1 as originally planned. As a result, it can be avoided to unnecessarily contact the used biosensor 2, and any infections caused by contacting the used biosensor 2 can be thereby prevented.

The plurality of acting portions 52A of the sliding block 52 in the disposal mechanism 5 are aligned in the shorter-dimension direction to be symmetrical to the center line L2 of the biosensor 2. Therefore, the biosensor 2 can be symmetrically subject to the load based on the center line L2 serving as a reference line, and the biosensor 2 can be thereby transported straight ahead along the disposal direction D1. More specifically, in the blood glucose level measuring device 1, the biosensor 2, when disposed of, is prevented from jumping out in any slantwise direction other than the D1 direction. This is another reason why the biosensor 2 can be disposed of as desired.

The present invention is not necessarily limited to the blood glucose level measuring device described so far, and can be variously modified. For example, the edge portions (contact points) in the plurality of terminals and the contact portions of the sliding block may be constituted as illustrated in FIGS. 10 to 12, or differently constituted.

In the example illustrated in FIG. 10A, contact points 64, 65, 65 and 67 of a plurality of terminals 60, 61, 62 and 63 in the connector portion are linearly aligned obliquely in directions D3 and D4 orthogonal to the disposal direction D1 (shorter-dimension direction of the biosensor 2).

In the plurality of terminals 60 to 63 thus constituted, when the biosensor 2 is transported in the D1 direction to be disposed of, the contact points 64 to 67 move away from the biosensor 2 one by one, starting from the contact point 64, contact point 65, contact point 66, and then, contact point 67 as illustrated in FIGS. 10B to 10E. Therefore, when the biosensor 2 is disposed of, all of the edge portions of the plurality of terminals 60 to 63 do not exert their elastic restoring force thereto at the same time, but exert each of them separately at a time. Further, the load of the sliding knob 52 acting on the biosensor 2 in the D1 direction (see FIGS. 3 to 7) can also be lessened. As a result, the biosensor 2 can avoid being subject to an excessively large load at once, which prevents the biosensor 2 from jumping out through the sensor insertion port 30 (see FIG. 1).

In the example illustrated in FIGS. 11A and 11B, the number of a plurality of terminals 70, 71, 72, 73 and 74 in the connector portion is an odd number, the terminal 72 in the center is provided along the center line L1 of the biosensor 2, and contact points 75, 76, 77, 78 and 79 of the plurality of terminals 70 to 74 are provided so as to have a symmetrical positional relationship relative to the center line L1. In the example illustrated in FIGS. 11A and 11B, wherein the contact points 75-79 of the plurality of terminals 70 to 74 are provided to be symmetrical to the center line L1, the biosensor 2 can avoid being subject to an excessively large load from the plurality of terminals 70 to 74 when the biosensor 2 is disposed of.

FIGS. 12A, 12B and 12C illustrate another example of the acting portion in the sliding block.

A sliding block 80 illustrated in FIG. 12A includes an acting portion 81. The acting portion 81 is provided so as to contact a center position of the biosensor 2 in the shorter-dimension directions D3 and D4.

In FIG. 12B, a sliding block 82 includes two acting portions 83. The acting portions 83 are provided to be symmetric to the center line L2 while avoiding the center line L2 of the biosensor 2 in the shorter-dimension directions D3 and D4.

In FIG. 12C, a sliding block 84 includes an acting portion 85. The acting portion 85 is not formed in a pin shape but is formed in a flat-plate shape, and a center line of the acting portion 85 in the shorter-dimension directions D3 and D4 is coincident or substantially coincident with the center line L2 of the biosensor 2 in the shorter-dimension directions D3 and D4.

In the examples illustrated in FIGS. 12A to 12C, the acting portions 81, 83 and 85 of the sliding blocks 80, 82 and 84 are adapted to symmetrically exert the load to the biosensor 2 relative to the center line L2 of the biosensor 2 in the shorter-dimension directions D3 and D4. Therefore, the biosensor 2, when disposed of, can be transported straight ahead along the disposal direction D1.

The present invention is not necessarily limited to the blood glucose level measuring device for measuring the blood glucose level, and is applicable to an analyzing device for measuring other elements such as cholesterol or lactic acid according to the electrochemical process.

The invention claimed is:

1. A connector device configured to receive an analytic instrument by the analytic instrument being inserted into the connector device in a direction along a first axis, the connector device comprising:
a first terminal configured to contact a first electrode of the analytic instrument when the analytic instrument is inserted into the connector portion, the first terminal having a first contact portion that contacts the first electrode and applies a first pressing force onto the first electrode; and
a second terminal configured to contact a second electrode of the analytic instrument when the analytic instrument is inserted into the connector portion, the second terminal having a second contact portion that contacts the second electrode and applies a second pressing force onto the second electrode,
wherein the first contact portion and the second contact portion are aligned in a direction that is not orthogonal to the first axis.

2. The connector device according to claim 1, further comprising:
a third terminal configured to contact a third electrode of the analytic instrument when the analytic instrument is inserted into the connector portion, the third terminal having a third contact portion that contacts the third electrode and applies a third pressing force onto the third electrode,
wherein the first contact portion, the second contact portion, and the third contact portion are not aligned in a direction that is orthogonal to the first axis.

3. The connector device according to claim 2, further comprising:
a fourth terminal configured to contact a fourth electrode of the analytic instrument when the analytic instrument is inserted into the connector portion, the fourth terminal having a fourth contact portion that contacts the fourth electrode and applies a fourth pressing force onto the fourth electrode,
wherein the first contact portion, the second contact portion, the third contact portion, and the fourth contact portion are not aligned in a direction that is orthogonal to the first axis.

4. The connector device according to claim 1, further comprising:
a disposal mechanism configured to dispose of the analytical instrument after analysis is complete.

5. The connector device according to claim 4, wherein the disposal mechanism is configured to push the analytical instrument out of the connector device in the direction along the first axis.

6. The connector device according to claim 1, wherein the first terminal includes a first flat spring that provides the first pressing force.

7. The connector device according to claim 6, wherein the second terminal includes a second flat spring that provides the second pressing force.

8. The connector device according to claim 1, wherein the first contact portion and the second contact portion are arranged to have a symmetrical or substantially symmetrical positional relationship relative to a center line of the analytical instrument, the center line of the analytical instrument extending parallel to the first axis.

9. The connector device according to claim 2, wherein the first contact portion, the second contact portion, and the third contact portion are arranged to have a symmetrical or substantially symmetrical positional relationship relative to a center line of the analytical instrument, the center line of the analytical instrument extending parallel to the first axis.

10. The connector device according to claim 3, wherein the first contact portion, the second contact portion, the third contact portion, and the fourth contact portion are arranged to have a symmetrical or substantially symmetrical positional relationship relative to a center line of the analytical instrument, the center line of the analytical instrument extending parallel to the first axis.

11. The connector device as claimed in claim 1, wherein the first contact portion and the second contact portion are linearly or substantially linearly aligned in a direction oblique to the first axis.

12. The connector device as claimed in claim 2, wherein
the first contact portion, the second contact portion, and the third contact portion are linearly or substantially linearly aligned in a direction oblique to the first axis.

13. The connector device as claimed in claim 4, wherein
the disposal mechanism includes one or a plurality of acting portions, the acting portions configured to contact the analytical instrument in order to apply a load directed in a disposal direction to the analytical instrument, the disposal direction being parallel to the first axis, and the one or plurality of acting portions are arranged so that the load can be applied to the analytical instrument symmetrically or substantially symmetrically based on a second center line serving as a reference line, the second center line extending in a thickness direction of the analytical instrument, the thickness direction of the analytical instrument being orthogonal to the first direction when the analytical instrument is inserted into the connector portion of the analytical instrument.

14. The connector device as claimed in claim 13, wherein at least one acting portion is placed on the second center line.

* * * * *